(12) United States Patent
Himmelbauer et al.

(10) Patent No.: US 7,913,552 B2
(45) Date of Patent: Mar. 29, 2011

(54) DEVICE FOR TESTING THE ADHESION OF A COATING TO A SUBSTRATE AND METHOD OF USING SAME

(75) Inventors: Dolph A. Himmelbauer, Cincinnati, OH (US); Scott E. Flegel, Twining, MI (US)

(73) Assignee: Random Logic, LLC, Cincinnati, OH (US)

( * ) Notice: Subject to any disclaimer, the term of this patent is extended or adjusted under 35 U.S.C. 154(b) by 461 days.

(21) Appl. No.: 12/200,966

(22) Filed: Aug. 29, 2008

(65) Prior Publication Data

US 2009/0114006 A1    May 7, 2009

Related U.S. Application Data

(60) Provisional application No. 60/985,348, filed on Nov. 5, 2007.

(51) Int. Cl.
*G01N 19/04*    (2006.01)
(52) U.S. Cl. .................................................. 73/150 A
(58) Field of Classification Search ................. 73/150 A
See application file for complete search history.

(56) References Cited

U.S. PATENT DOCUMENTS

| | | | |
|---|---|---|---|
| 2,353,852 A | 7/1944 | Rowland et al. | |
| 3,871,940 A | 3/1975 | Antonioni | |
| 4,803,872 A | 2/1989 | Crawford et al. | |
| 4,888,985 A * | 12/1989 | Siemer ........................ | 73/150 A |
| 4,893,503 A * | 1/1990 | Kimura et al. .............. | 73/150 A |
| 5,325,713 A | 7/1994 | Furst et al. | |
| 6,230,548 B1 | 5/2001 | Han et al. | |
| 6,408,678 B1 * | 6/2002 | Chopra et al. ...................... | 73/9 |
| 6,474,140 B1 | 11/2002 | Han et al. | |
| 6,584,858 B1 * | 7/2003 | Miyazawa et al. .............. | 73/827 |
| 6,896,734 B2 | 5/2005 | Nishioka et al. | |
| 2007/0107828 A1 | 5/2007 | Barker et al. | |

* cited by examiner

*Primary Examiner* — Hezron Williams
*Assistant Examiner* — Nathaniel Kolb
(74) *Attorney, Agent, or Firm* — Fraser Clemens Martin & Miller LLC; J. Douglas Miller

(57) ABSTRACT

A device for testing the adhesion of a coating to a substrate and a method of using the device are disclosed. The device is adapted to substantially replicate and consistently conduct the adhesion test procedure described in ASTM standards D3359 and F1842. The device includes a support with a source of a pressure sensitive adhesive tape rotatably mounted to the support. A tape dispenser and means to cause the tape to contact a test surface are mounted to the support. Means to remove the tape from the test surface is provided that includes a take-up spool adapted to receive the tape removed from the test surface.

19 Claims, 7 Drawing Sheets

DEVICE FOR TESTING THE ADHESION OF A COATING TO A SUBSTRATE AND METHOD OF USING SAME

CROSS-REFERENCE TO RELATED APPLICATION

This application claims the benefit of U.S. Provisional Patent Application Ser. No. 60/985,348 filed on Nov. 5, 2007, hereby incorporated herein by reference in its entirety.

FIELD OF THE INVENTION

The present invention relates to a device and a test method for evaluating the adhesion of coatings such as inks or paints, for example, to a surface of a substrate, and more specifically to a device and a method which automates and mechanizes the adhesion test procedure described in standards such as ASTM D3359 and F1842.

BACKGROUND OF THE INVENTION

When applying a coating such as ink, paint, or varnish for example, to a substrate, it is typically important that the coating be adequately adhered to the surface of the substrate to which it is applied. This is especially important in industries such as printing, painting, and converting related industries. During the manufacturing process in these types of industries, many factors can affect the adhesive strength of the bond between the inks, paints, and other coatings, and the surface of the substrate. Thus, it is necessary to test the adhesion during the manufacturing/printing/painting/converting process to confirm that a desired level of adhesion is obtained. A standard test, commonly termed a tape test and described in ASTM test standards D3359 and F1842, as well as other test standards such as ISO 2409, for example, has been developed for evaluating the adhesive strength of the bond between the inks, paints, and coatings and the surface of the substrate.

The tape test is performed by applying a strip of tape to the coated surface, removing it, and visually evaluating the amount of coating that has been removed by the tape. In the standard test, the tape is both applied and removed by hand. In cases where the coating has ingredients that create a slick or difficult to bond surface, the surface can be prepared by cutting through or "cross-hatching" the coating in a criss-cross pattern with a sharp knife edge. It is generally accepted in the printing, painting, and converting industries that the adhesion of the coating to the surface of the substrate can be evaluated employing the tape test.

In the course of performing and observing thousands of tape tests, the inventors have determined that the human controlled motions in the tape test have a significant impact on the final results. The variability of these human motions can produce widely varying results from test specimens that would otherwise be observed as having a substantially equivalent bond strength. For example, if the tape is applied to the coated surface with the palm of a hand for one test, with a thumb in another test, with a pencil eraser in another (as suggested in some standards), and with a fingernail or other solid surface in yet another test, each application method may create a different bond strength between the adhesive of the tape and the surface being evaluated, resulting in different results from each test.

Additionally, the rate at which the tape is removed from the surface being tested and the angle at which the tape is pulled in respect of its applied position are known to significantly influence the results of the test. The referenced ASTM standards suggest pulling the tape off 180 degrees from itself rapidly (not jerked). However, this method is not always followed by a person performing the test.

The strength of the bond between the coating and the surface of the substrate is frequently incorrectly reported as a result of the variability in the hand application and the hand removal of the tape. This may cause the printer/manufacturer to either make adjustments to the process of applying the coating when none are needed, or fail to recognize when adjustments to the process are needed. In either case, unreliable or unrepeatable results from the tape test may create costly manufacturing errors.

It would be desirable to provide a device that facilitates consistently applying a tape to and removing the tape from a coated surface of a substrate to evaluate the adhesive strength of the bond between the coating and the substrate.

SUMMARY OF THE INVENTION

Compatible and attuned with the present invention, a device that facilitates consistently applying a tape to and removing the tape from a coated surface of a substrate to evaluate the adhesive strength of the bond between the coating and the substrate, has surprisingly been discovered.

In one embodiment, a device for testing the adhesion of a coating to a substrate comprises a support; a source of a pressure sensitive adhesive tape mounted to the support; a tape dispenser; means to cause the tape to contact a test surface; and means to remove the tape from the test surface.

In another embodiment, a device for testing the adhesion of a coating to a substrate a support; a dispensing spool rotatably mounted on the support and adapted to receive a roll of a pressure sensitive adhesive tape; a tape dispenser adapted to dispense a length of the tape from the dispensing spool; the dispenser including a slidable plate, a pinion gear, and a brush mounted thereto; and a rack to provide a defined path of travel for the plate, wherein the rack and the pinion gear cooperate to cause a rotation of the brush upon movement of the plate; the brush causing the tape to contact a test surface disposed between the sidewalls of the support; and means to remove the tape from the test surface including a take-up spool having a drive gear and an associated gear segment, the gear segment engaged with the drive gear to cause rotation of the take-up spool to remove the tape from the test surface, the take-up spool receiving the tape removed from the test surface.

In another embodiment, a method for conducting an adhesion test comprises the steps of providing a testing device having a support; a source of a pressure sensitive adhesive tape mounted to the support; a tape dispenser; means to cause the tape to contact a test surface; and means to remove the dispensed tape from the test surface; dispensing the length of tape from the source; positioning the testing device to cause an adhesive side of at least a portion of the length of dispensed tape to contact the test surface; forcing the adhesive side of the tape against the test surface; and removing the length of tape from the test surface.

BRIEF DESCRIPTION OF THE DRAWINGS

The above, as well as other advantages of the invention, will become readily apparent to those skilled in the art from the following detailed description of an embodiment of the invention when considered in the light of the accompanying drawings, in which.

DETAILED DESCRIPTION OF THE PREFERRED EMBODIMENT

The following detailed description and appended drawings describe and illustrate various exemplary embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Figure 1:
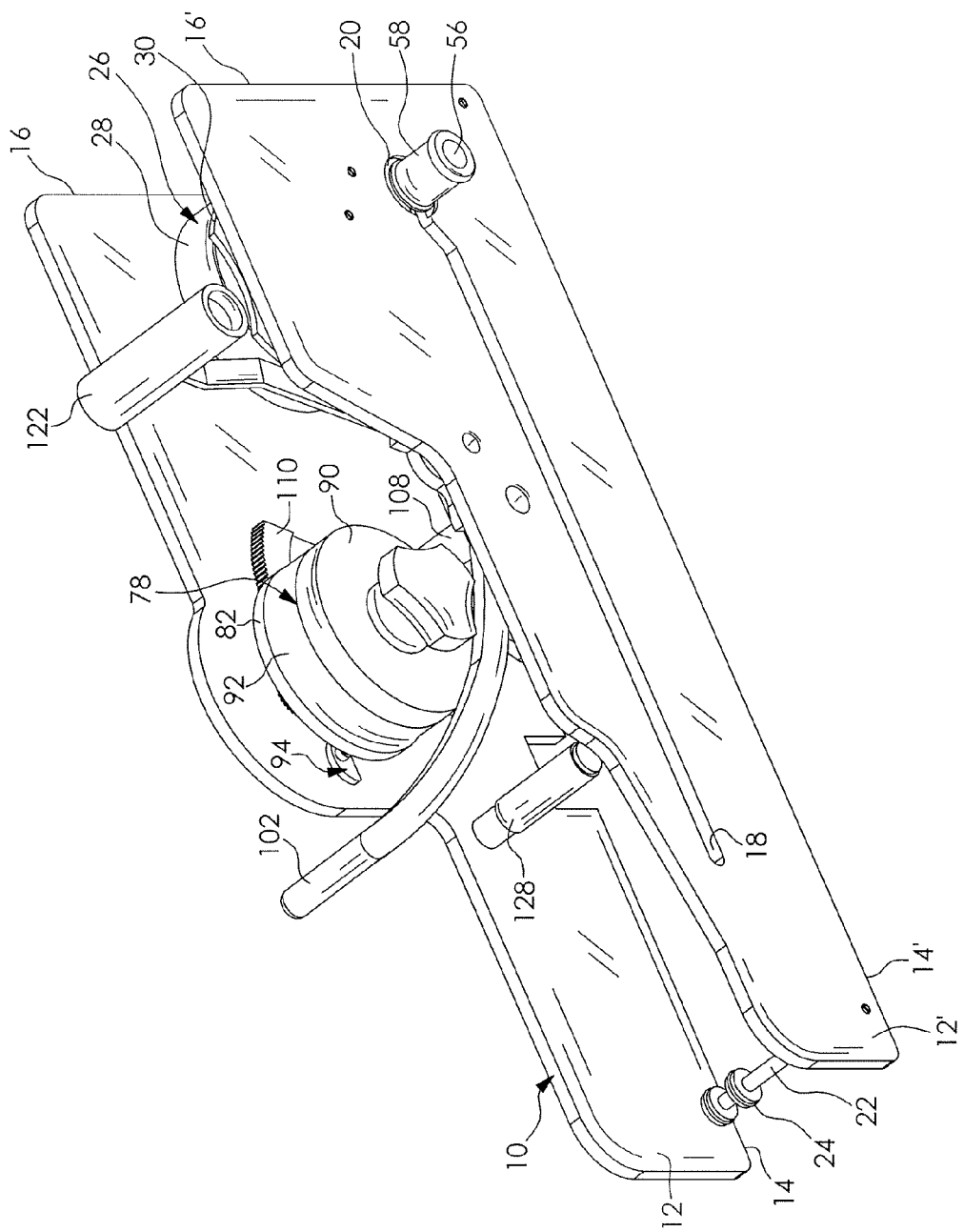
FIG. 1 is a perspective view of a device for testing the adhesion of a coating to a surface of a substrate according to an embodiment of the invention.
Figure 2:
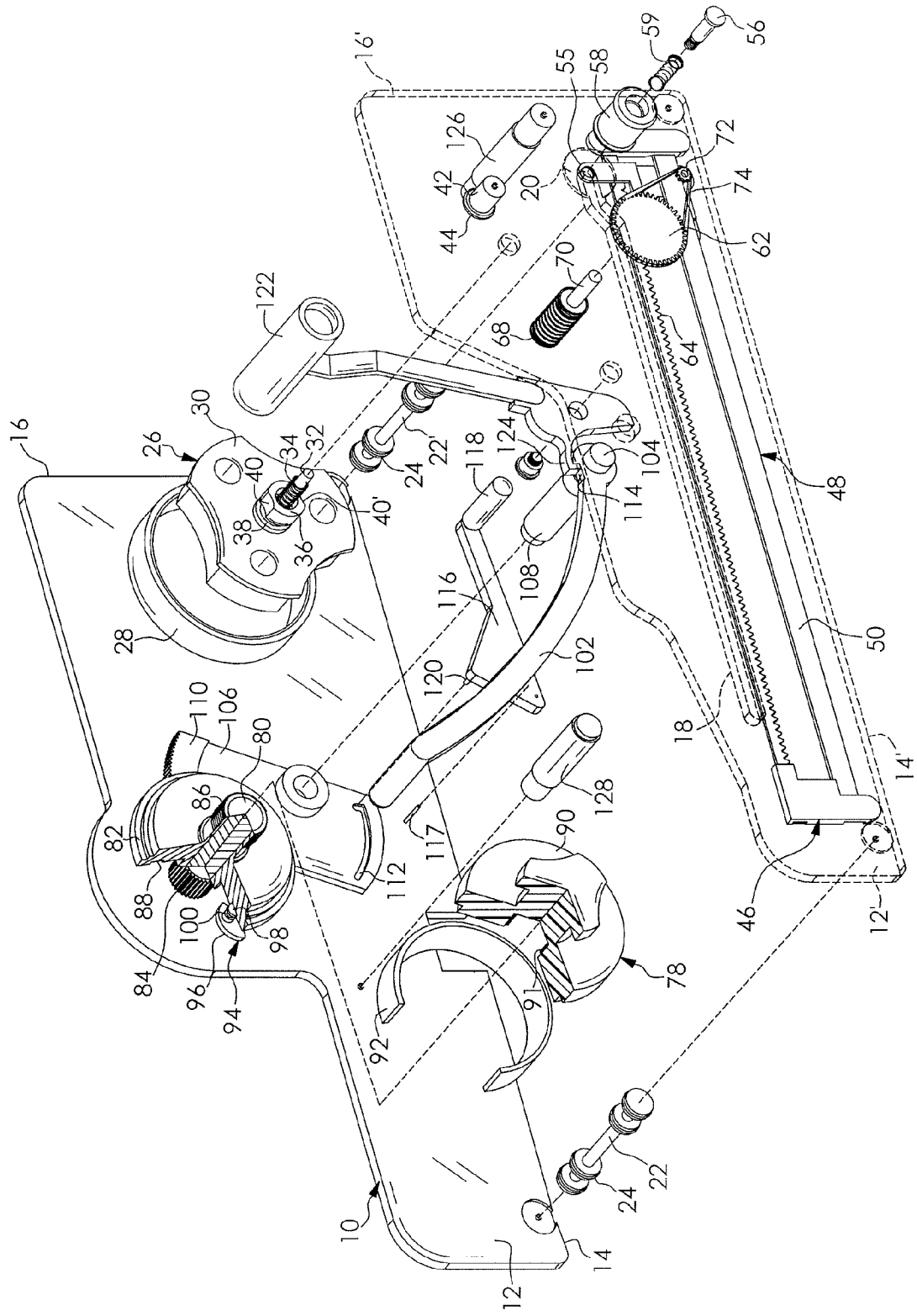
FIG. 2 is an exploded perspective view in partial section of the device illustrated in FIG. 1.
Figure 3:
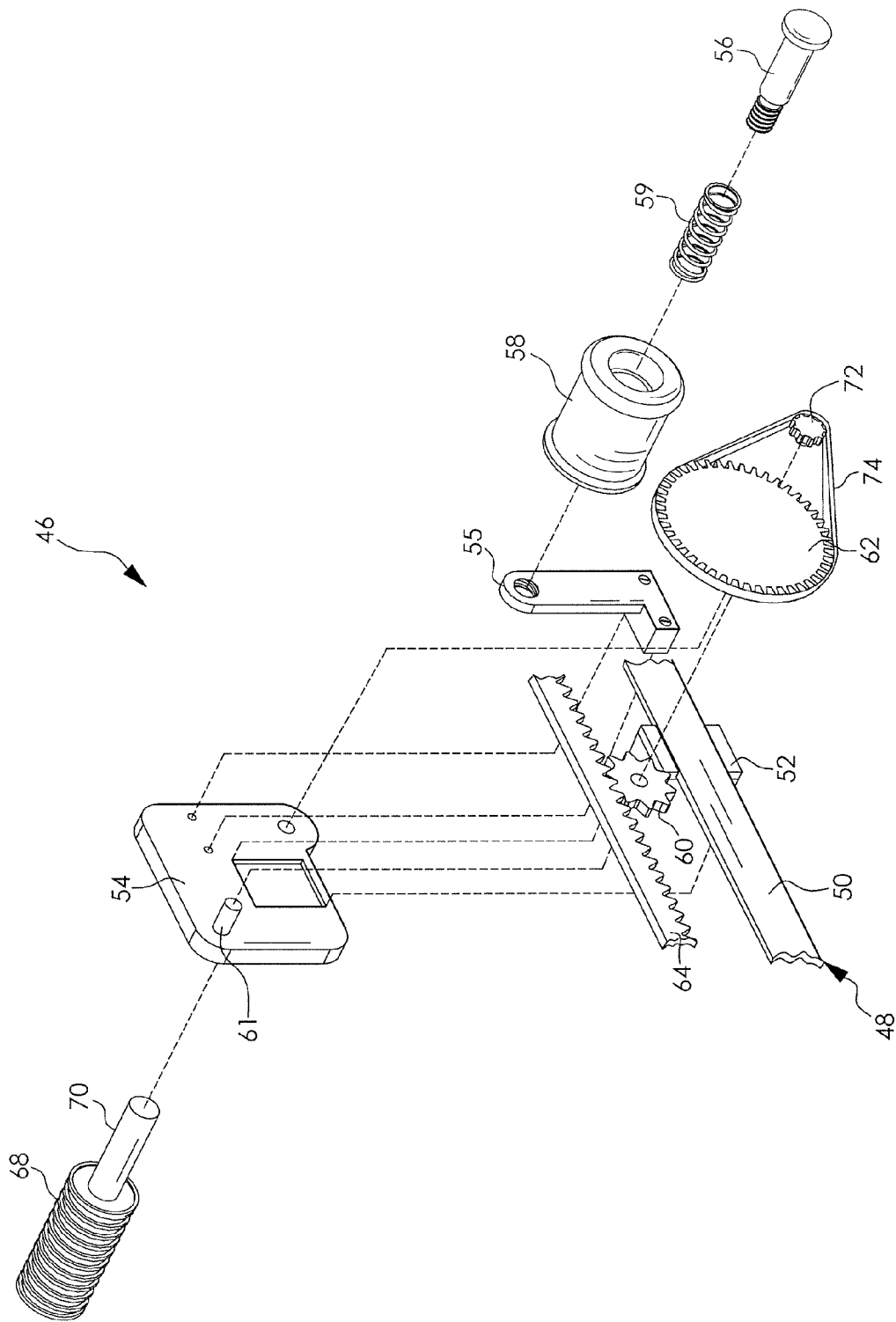
FIG. 3 is an enlarged exploded perspective view of a slide assembly the device illustrated in FIG. 2.

Referring to FIGS. 1-3, a device for testing the adhesion of a coating to a substrate is illustrated. The coatings may include chemicals such as UV curable, conventional water or oil based primers, inks, paints, varnishes and the like; and may be applied by processes including lithographic, flexographic, gravuer, and digital printing, spraying, powder coating, dipping, and rolling, for example. The substrate may include materials such as metals, woods, plastics, (polypropylene, polystyrene, PVC,), and the like. However, it should be understood that the device can be employed to test the adhesion between other coatings and substrates as desired. The device provides a mechanical method for both applying and removing a pressure sensitive adhesive tape to a test surface in a manner that is substantially compliant with ASTM standards D3359 and F1842, and other tape test standards.

The device includes a support frame 10 having a pair of spaced apart sidewalls 12, 12'. The sidewalls 12, 12' have substantially matching straight edges 14, 14' and 16, 16', respectively. A generally elongate slot 18 is formed in the sidewall 12' substantially parallel to edge 14'. A recess 20 is formed in the sidewall 12' at one end of the slot 18 adjacent the edge 16'. At the one end of the slot 18 adjacent the recess 20, the slot 18 diverges to a location wherein a distance between the slot 18 and the edge 14' is greater at the one end than the distance between the slot 18 and the edge 14' at the opposite end. Shafts 22, 22' are disposed between the sidewalls 12, 12' and attached thereto adjacent edges 14, 14' to maintain the sidewalls 12, 12' in a spaced apart relation and to contact the test surface. The shafts 22, 22' may include one or more gripping members 24 such as an O-ring, for example, to facilitate the device stably resting on the test surface. In the illustrated embodiment the shafts 22, 22' are secured to the sidewalls 12, 12' with threaded fasteners. It should be understood that the shafts 22, 22' can be secured by any suitable means such as a rivet, or by a welding or employing an adhesive, for example.

A source 26 of a pressure sensitive tape 28 is mounted between the sidewalls 12, 12'. Typically a semi-transparent pressure sensitive tape is employed such as a 3M® or a Scotch® brand 600, 610, and 810 tapes, for example. In the illustrated embodiment, the source 26 includes a dispensing spool 30 rotatably received on a shaft 32 mounted on the sidewall 12'. Favorable results have been obtained employing a dispensing spool 30 adapted to receive roll of tape 28 having a spool core with an inside diameter of about 3.0 inches. However, it should be understood that the spool 30 can be adapted to receive spool cores having other diameters.

A compression spring 34 is disposed on the shaft 32 between the sidewall 12' and the spool 30 to maintain the spool 30 in spaced apart relation in respect of the sidewall 12'. The spool 30 includes a hub 36 extending from a side thereof. An annular groove 38 is formed in the hub 36. A pair of opposing generally arcuate shaped slots 40, 40' is formed in the hub 36 extending from an end of the hub 36 to the groove 38. A spool lockout 42 is mounted to the sidewall 12' adjacent the shaft 32. The lockout 42 includes an annular end 44 disposed between the sidewall 12' and the hub 36. The end 44 is adapted to be received by the slots 44, 44' and engage the groove 38 of the hub 30. When the end 44 is engaged with the groove 38, the spool 30 is maintained in a position closer to sidewall 12' in respect of the normal position to provide for the receipt of the roll of the pressure sensitive tape 28 between the spool 30 and the sidewall 12, which facilitates placing the roll of the pressure sensitive tape 28 on the spool 30.

A tape dispenser 46, more clearly illustrated in FIGS. 2-3, is mounted between the sidewalls 12, 12'. The tape dispenser 46 includes a slide assembly 48 having a rail 50 and a sliding member 52 disposed thereon. The slide assembly 48 is mounted to the sidewall 12' adjacent to and substantially parallel with the slot 18. Favorable results have been obtained by pivotally mounting the slide assembly 48 to the sidewall 12' at an end adjacent shaft 22 and slidably mounting the slide assembly 46 at an opposite end adjacent shaft 22 to enable the slide assembly 48 to pivot about the end of the slide assembly 48 adjacent shaft 22. Additionally, favorable results have been obtained employing the slide assembly LWLC9B manufactured by IKO and available for purchase from Motion Industries located at 1605 Alton Road, Birmingham, Ala. 35210. A plate 54 is attached to the sliding member 52. A bracket 55 is attached to the plate 54 adapted to threadably receive a shaft 56, which extends through the slot 18 formed in the sidewall 12'. The shaft 56 has an annular handle 58 disposed thereon adjacent the end extending through the slot 18. A spring 59 is disposed on the shaft 56 between the handle 58 and the shaft 56 to bias the handle 58 toward the sidewall 12' and cause an end of the handle 58 to be received in the recess 20 formed in the sidewall 12'. When the end of the handle 58 is received in the recess 20, the sliding member 52 is maintained at the one end of the slot 18.

A pinion gear 60 is attached to a shaft 61 rotatably mounted to the plate 54. In the illustrated embodiment, a second gear 62 is mounted to the distal end of the shaft 61. The second gear 62 has a diameter larger than the diameter of the pinion gear 60 and adapted to rotate with the pinion gear 60. The tape dispenser 46 includes a rack 64 attached to an inside surface of the sidewall 12' adjacent and substantially parallel with the rail 50 of the slide assembly 48. The pinion gear 60 is engaged with the rack 64.

Means to cause the tape 28 to contact the test surface and press the adhesive side of the tape 28 against the test surface is mounted to the plate 54 of the tape dispenser 46. In the illustrated embodiment, the means is a generally cylindrically shaped brush 68 received on a shaft 70 rotatably attached to the plate 54. Favorable results have been obtained by employing a brush having helically mounted bristles available from the Carolina Brush Company located in Gastonia, N.C. It should be understood that brushes having other shapes and configurations such as a non-rotating brush, can be employed.

Additionally, it should be understood that when the handle 58 is at the one end of the slot 18 having the greater distance between the slot 18 and the edge 14', the slide assembly 48 is caused to pivot about the opposite end adjacent shaft 22, which lifts the brush 68 in respect to the test surface and defines an end of the portion of tape 28 that is adhered to the test surface. A drive gear 72 is affixed to an end of the shaft 70. A drive belt 74 is attached to the drive gear 72 and the second gear 62 to provide a rotation of the brush 68 upon a movement of the plate 54 in respect of the rack 64. Favorable results have been obtained employing a one-way locking steel needle-roller bearing to mount the second gear 62 to the shaft 61 to cause the brush 68 to rotate upon the movement of the plate 54 toward the recess 20. Such one-way locking bearings are available from McMaster-Carr located in Aurora, Ohio.

Means to remove the tape 28 from the test surface is mounted between the sidewalls 12, 12'. The means includes a take-up spool assembly 78 rotatably received on a shaft 80 mounted to the sidewalls 12. The take-up spool 78 is adapted to windably receive the tape 28 dispensed from the source 26. A drive gear 84 is attached to an end of the shaft 80 adjacent the sidewall 12. The take-up spool 78 includes a disk 82 having one side abut the drive gear 84 and an opposite side including a threaded member 86 extending therefrom. An annular groove 88 is formed in the one side of the disk 82. Favorable results have been obtained employing a one-way locking steel needle-roller bearing to mount the disk 82 to the shaft 80 to cause the take-up spool 78 to rotate only upon the rotation of the drive gear 84 and the shaft 80 assembly in one direction. Such one-way locking bearings are available from McMaster-Carr located in Aurora, Ohio. A retaining disk 90 is provided having a threaded bore 91 to threadably receive the threaded member 86 of the disk 82. In the illustrated embodiment the retaining disk 90 is formed from a plastic material or the like. It should be understood that other suitable material can be employed to form the retaining disk 90, as desired. The disk 82 and the retaining disk 90 cooperate to removably receive and secure a spool core 92 therebetween for windably receiving the tape 28. Favorable results have been obtained using a spool core formed from a cardboard such as those available for purchase from Ox Paper Tube & Core of Hanover, Pa.; or Merrimac Spool & Reel Co. of Haverhill, Mass. Additionally, favorable results have been obtained employing a disk 82 and a retaining disk 90 adapted to receive a spool core 92 having an inside diameter of about 2.5 inches. However, it should be understood that the disks 82, 90 can be adapted to receive spool cores having other diameters.

A spool brake assembly 94 is provided to militate against an undesired rotation of the take-up spool 78. The spool brake assembly 94 includes a brake plate 96 pivotally mounted to the sidewall 12 adjacent the take-up spool 78. A sleeve 98 is rotatably mounted on a shaft (not shown) disposed on and extending from the plate 96. Favorable results have been obtained employing a one-way locking steel needle-roller bearing to mount the sleeve 98 on the shaft (not shown) to only allow the sleeve 98 to rotate in one direction in respect of a longitudinal axis of the shaft. Such one-way locking bearings are available from McMaster-Carr located in Aurora, Ohio. One end of the sleeve 98 extends into the annular groove 88 formed in the disk 82 of the take-up spool 78. At least one O-ring 100 is disposed on the sleeve 98 adjacent the one end, wherein the O-ring 100 is caused to contact a surface of the annular groove 88, and a friction therebetween militates against an undesired rotation of the take-up spool 78. It should be understood that the brake plate 96 can be pivoted to provide a selected contact force between the O-ring 100 and the surface of the annular groove 88.

A take-up lever 102 is mounted between the sidewalls 12, 12'. The take-up lever 102 is attached to a shaft 104 having ends pivotally mounted to the sidewalls 12, 12', respectively. A plate 106 is attached to the shaft 104 adjacent sidewall 12 and spaced apart from the take-up lever 102. A roller guide 108 is disposed on the shaft 104 between the take-up lever 102 and the plate 106. The plate 106 includes a gear-segment 110 disposed on one end and a groove 112 formed therein adjacent an opposite end. The gear-segment 110 is engaged with the drive gear 84 mounted on the shaft 80 to cause a rotation of the take-up spool 78 upon a downward movement of the take-up lever 102. A notch 114 is formed in the take-up lever 102 adjacent the pivot point.

An arm 116 is pivotally mounted at one end on a pin 117 extending outwardly from the sidewall 12, the pin 117 adjacent the end of the plate 106 having the groove 112. A roller guide 118 is rotatably disposed on an opposite end of the arm 116. A pin 120 is disposed on the arm 116 and extends therefrom with a distal end of the pin 120 received within the groove 112 formed in the plate 106. The pin 120 and the groove 112 cooperate to cause the arm 116 to pivot between a first position and a second position upon a movement of the take-up lever 102.

A release lever 122 is pivotally mounted between the sidewalls 12, 12'. The release lever 122 includes a hook member 124 formed at one end adjacent the pivot point. The hook member 124 is adapted to engage the notch 114 of the take-up lever 102 and maintain the take-up lever 102 in a normally locked position. A downward movement of the release lever 122 causes the hook member 124 to disengage the notch 114, releasing the take-up lever 102 from the normally locked position.

Roller guides 126, 128 are mounted between the sidewalls 12, 12' to guide the tape 28 from the source 26 to the dispenser 46; and from the dispenser 46 to the take-up spool 78, respectively. In the illustrated embodiment the guides are nylon cylindrical rollers rotatably mounted on shafts. It should be understood that other materials can be employed to form the rollers, and other shapes and types of guides can be employed, as well as additional or fewer number of guides, can be employed as desired. Additionally, in the illustrated embodiment the roller guides 126, 128 are secured to at least one of the sidewalls 12, 12' with threaded fasteners. It should be understood that the roller guides 126, 128 can be secured to the sidewalls 12, 12' by any suitable means such as a rivet, or by a welding or employing an adhesive, for example.

In use, the dispensing spool 30 of the testing device is urged toward sidewall 12' to cause the annular end 44 of the spool lockout 42 to pass through one of the slots 40, 40' formed in the hub 36 and be received in the groove 38 formed in the hub 36. The annular end 44 of the spool lockout 42 and the groove 38 cooperate to hold the spool 30 adjacent the sidewall 12' while a roll of the tape 28 is disposed on the spool 30. The spool 30 is rotated to release the spool 30 from the spool lockout 42 after the roll of the tape 28 is disposed on the spool 30.

An end of the tape 28 is pulled from the roll to dispense a length necessary to thread the tape 28 through the sequence of the roller 126; the brush 68; the roller 118; the roller 108; the roller 128; and attach the end of the tape 28 to the spool core 92 of the take-up spool 78, as illustrated in FIGS. 4-7. In the illustrated embodiment, the pressure sensitive adhesive of the tape 28 is employed to attach the end of the tape 28 to the spool core 92 of the take-up spool 78. However, it should be understood that the take-up spool 78 can be provided with other means to secure the end of the tape 28 thereto such as a hook or a cleat, for example. Additionally, it should be understood that the roll of the tape 28 is oriented on the spool 30 to cause the adhesive side of the tape 28 to face outwardly from the spool 30 and in position to contact the test surface 130.

Figure 4:
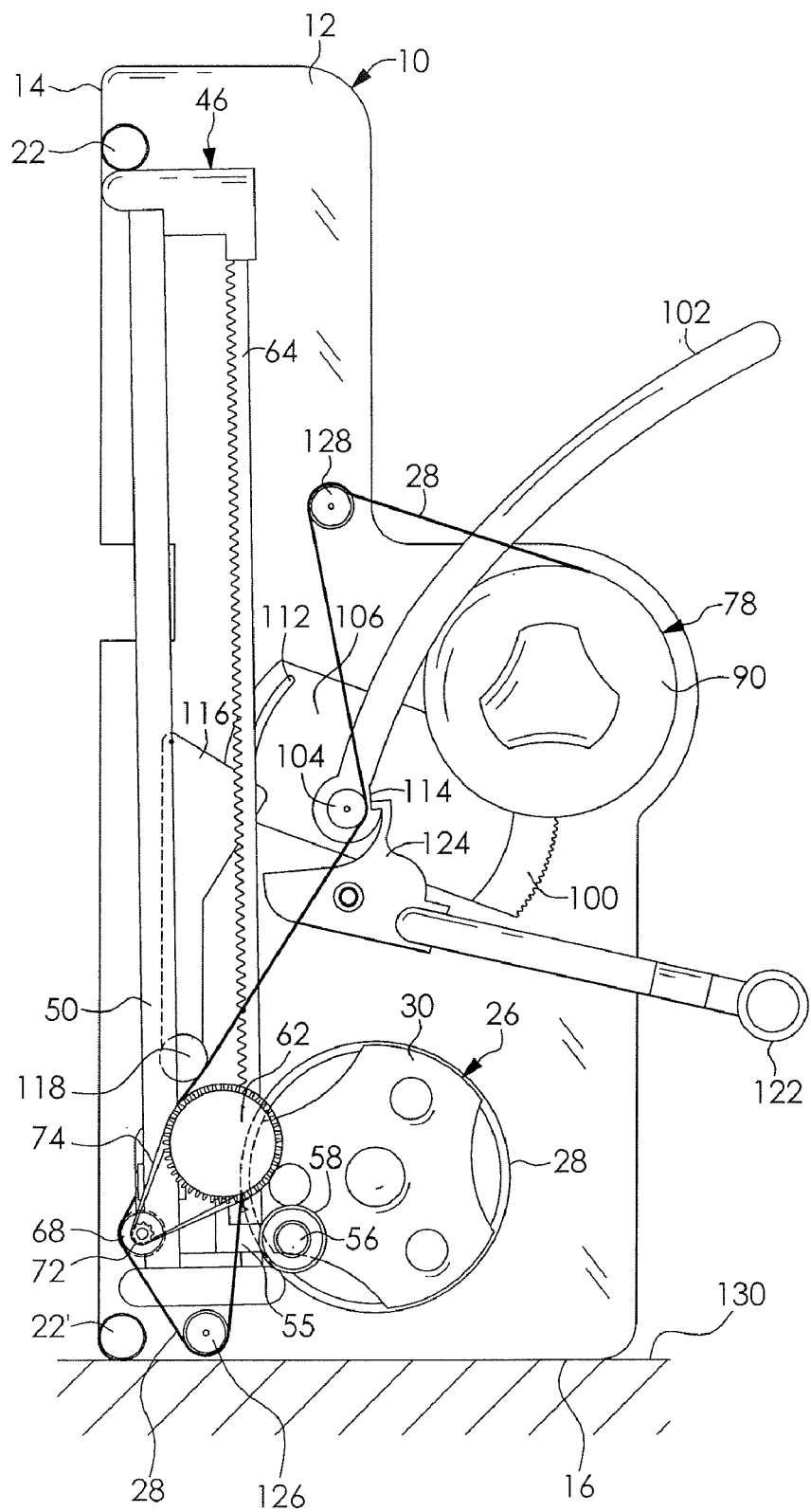
FIG. 4 is a schematic side elevational view of the device illustrates in FIG. 1 showing a step of using the device.
Figure 5:
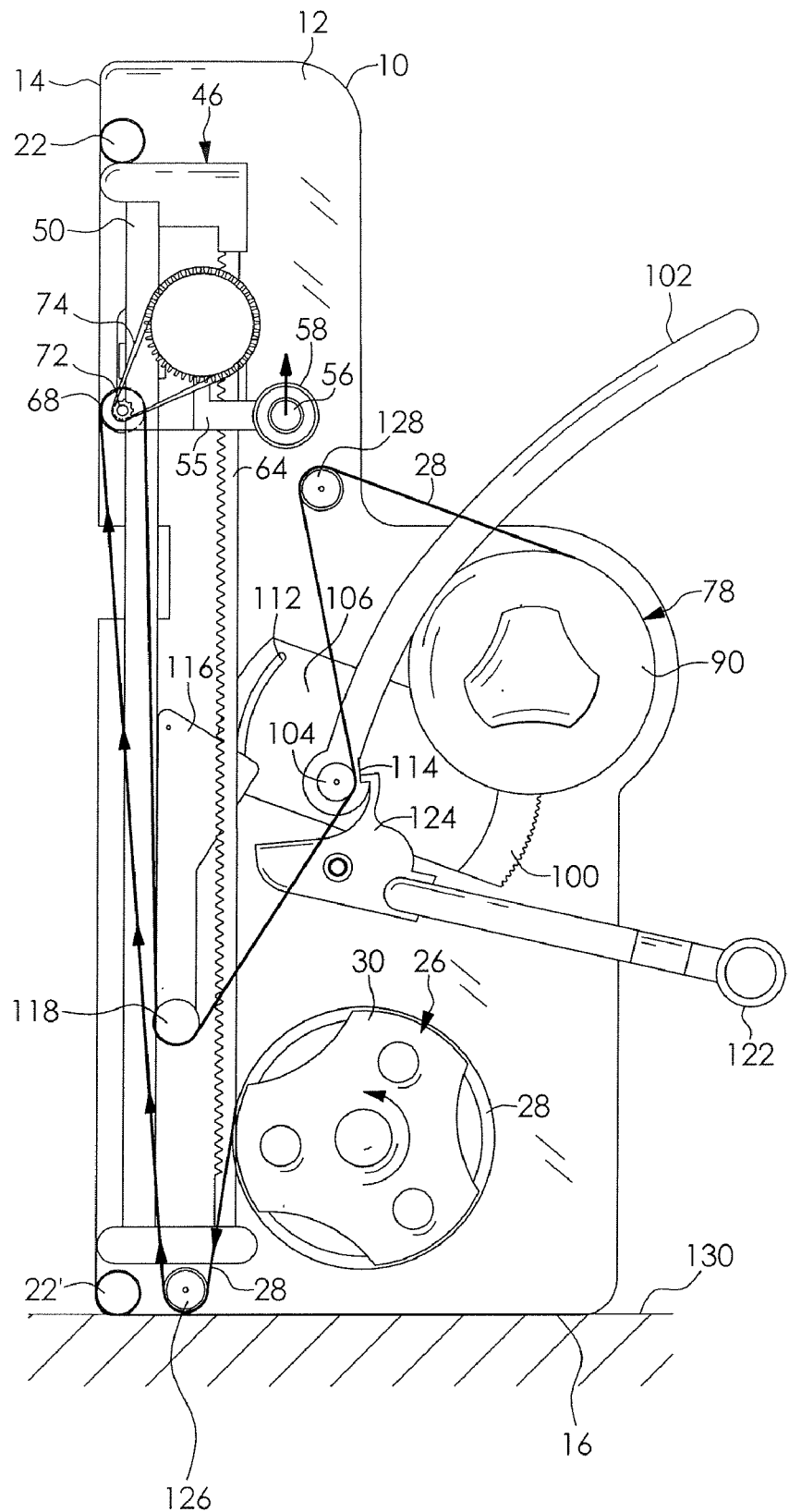
FIG. 5 is a schematic side elevational view of the device illustrates in FIG. 1 showing another step of using the device.

The testing device is typically placed on edges 16, 16' as shown in FIG. 4. The tape dispenser 46 is employed to dispense a length of the tape 28 from the spool 30. An end of the handle 58 is received within the recess 20 to secure the sliding member 52 of the tape dispenser 46 in a first position. A user grasps the handle 58; urges the handle 58 outwardly from the sidewall 12' to release the handle 58 from the recess 20; and moves the handle 58 to a second position at the opposite end of the slot 18, as shown in FIG. 5. By moving the handle 58 to the second position, the brush 68 pulls a length of the tape 28 from the spool 30. The length of the tape 28 is positioned between the edges 14, 14' of the sidewalls 12, 12', respectively, with the adhesive side of the tape 28 facing away from the testing device and in a position to be applied to the test surface 130. The tape dispenser 46 evenly dispenses the tape 28 from the spool 30 to facilitate an even distribution of the adhesive on the tape 28 that is dispensed. The tape dispenser 46 provides a length of the tape 28 for conducting the test having the adhesive freshly exposed to the atmosphere. The even distribution of the adhesive and freshly exposed adhesive facilitates a consistency of the condition of the adhesive on the tape 28 from test to test. It should be understood that the handle 58 may be moved to a selected position between the respective ends of the slot 18 to dispense a selected length of the tape 28.

Figure 6:
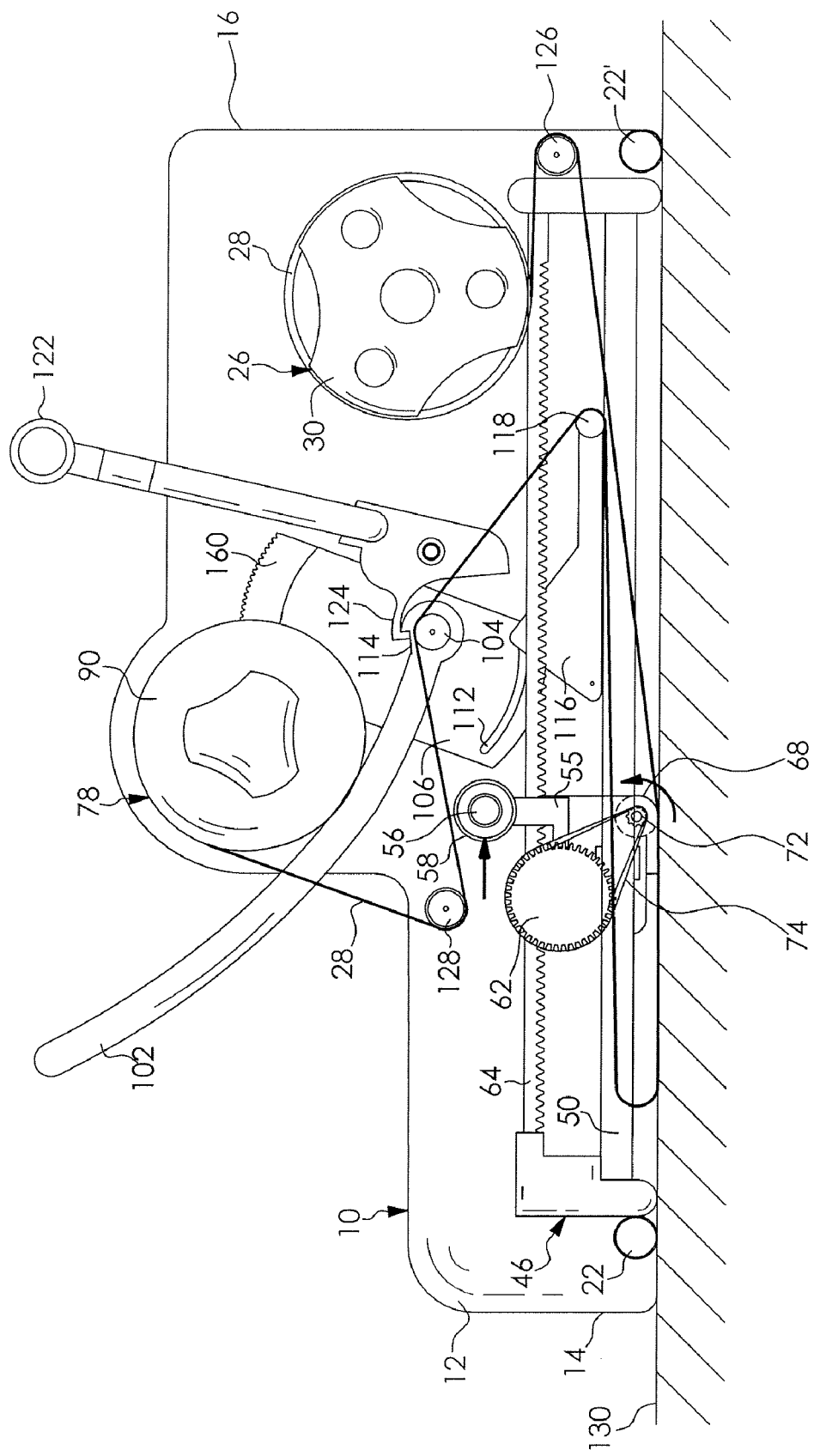
FIG. 6 is a schematic side elevational view of the device illustrates in FIG. 1 showing another step of using the device.
Figure 7:
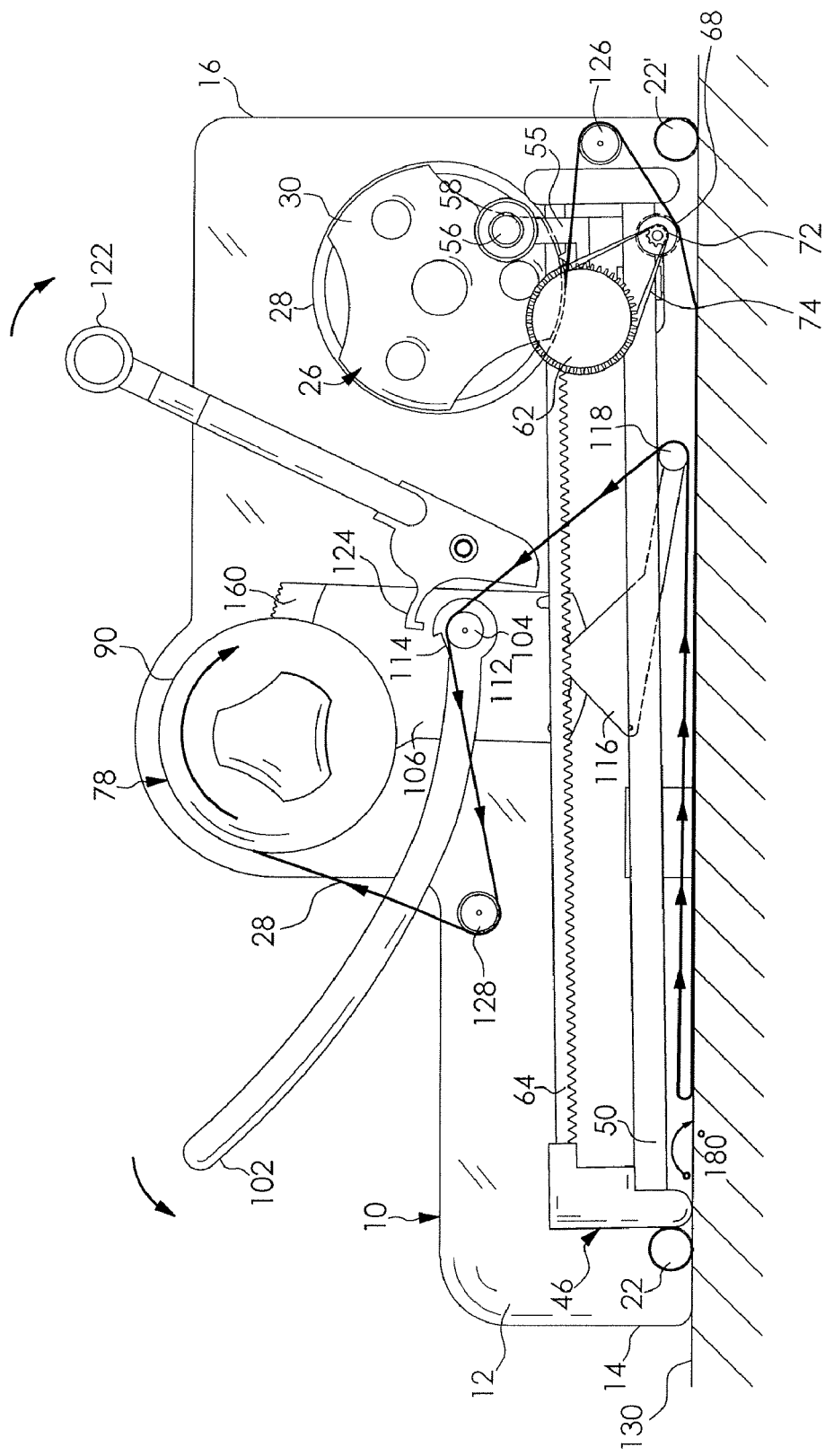
FIG. 7 is a schematic side elevational view of the device illustrates in FIG. 1 showing another step of using the device.

The edges 14, 14 of the testing device are placed on the test surface 130, as illustrated in FIGS. 6-7. In this position, the adhesive side of the tape 28 is facing and typically in contact with the test surface 130. The bristles of the brush 68 are in contact with the non-adhesive side of the tape 28 and apply a force thereto to press the adhesive side of the tape 28 against the test surface 130. The user grasps the handle 58 and slides it to the first position where the handle 58 is received in the recess 20. While moving the handle 58 to the first position, the rack 64 and the pinion gear 60, together with the second gear 62, the drive gear 72, and the drive belt 74, cause the brush 68 to rotate in a direction counter to the direction of travel of the handle 58. It should be understood that the brush 68 can be adapted to rotate in the same direction as the direction of travel of the handle 58. The rotation of the brush 68 and the helically disposed bristles facilitates a removal of air between the tape 28 and the test surface 130. Additionally, the position of the outside diameter of the brush 68 in respect to the test surface 130 causes the brush 68 to provide a substantially consistent force to press the adhesive side of the tape 28 against the test surface 130. The combination of the substantially consistent rotation of the brush 68 during the application of the tape 28 to the test surface 130 and the substantially consistent application force provided by the helix-wound bristles of the brush 68 provides a substantially repeatable means of applying the tape 28 to the test surface 130, thus facilitating the repeatability of the tape test. Although favorable results have been obtained by dispensing the tape 28 while the device is resting on the edges 16, 16' of the sidewalls 12, 12', it should be understood that the tape 28 may be dispensed while the edges 14, 14' are resting on the test surface 130, or are elevated slightly in respect of the test surface 130.

To remove the tape from the test surface 130, the user simultaneously grasps the take-up lever 102 with one hand and the release lever 122 with the other hand. The user urges the release lever 122 toward the test surface 130 causing the hook member 124 to disengage the notch 114 formed in the take-up lever 102 releasing the take-up lever 102 from the normally locked position. The user can then urge the take-up lever 102 toward the test surface 130 to cause the plate 106 attached thereto to pivot about the longitudinal axis of the shaft 104. The pivoting of the plate 106 causes the arm 116 to pivot downward to the second position as the pin 120 slides within the groove 112 of the plate 106 placing the roller 118 adjacent the test surface 130, as shown in FIG. 7. The gear segment 110 of the pivoting plate 106 is engaged with the drive gear 84 on the shaft 80 for the take-up spool 78 and causes the take-up spool 78 to rotate as the take-up lever 102 is urged toward the test surface 130. The rotating take-up spool 78 pulls the tape 28 from the test surface 130. The roller 118, being in the second position, causes the tape 28 to be removed from the test surface 130 at about 180 degrees from its direction of application, as recommended in ASTM standards D3359 and F1842. The use of both the take-up lever 102 and the release lever 122 requires a user to employ both hands to conduct the test, which facilitates a stability of the testing device on the test surface 130 during the test. Additionally, the take-up lever 102, together with the gear segment 110 and drive gear 84 facilitate pulling the tape 28 from the test surface at a consistent (not jerked) and rapid rate, which facilitates the repeatability and reliability of the test results. After the tape 128 has been removed from the test surface and received on the spool core 92, the levers 102, 122 are returned to the initial positions illustrated in FIGS. 4-6. The one-way locking steel needle-roller bearing enables the take-up lever 102 to be returned to the normally locked position without causing a rotation of the take-up spool 78.

The tape 28 received on the spool core 92 may be inspected for any coating adhered thereto that was removed from the substrate. It should be understood that the test surface 130 can also be inspected for coating that has been removed from the substrate. Employing the standards described in ASTM standards D3359 and F1842, the amount of coating removed from the substrate can be evaluated to provide a rating for the strength of the adhesion of the coating to the substrate. The rating can be used to determine if adjustments should be made to a manufacturing process disposing the coating on the substrate. Additionally, it has been found that the spool core 92 is a convenient means to store the tape 28 used for testing. New spool cores 92 can be employed for each test or for each series of tests, for example.

The testing device facilitates consistently applying the tape 28 to and removing the tape 28 from a coated surface of a substrate to evaluate the adhesive strength of the bond between the coating and the substrate. The testing device substantially mechanizes the "tape test" described in ASTM standards D3359 and F1842 to minimize variability in conducting the test.

From the foregoing description, one ordinarily skilled in the art can easily ascertain the essential characteristics of this invention, and without departing from the spirit and scope thereof, can make various changes and modifications to the invention to adapt it to various usages and conditions.

What is claimed is:

1. A device for testing the adhesion of a coating to a substrate comprising:
   a support;
   a source of a pressure sensitive adhesive tape mounted to the support;
   a tape dispenser including a brush that travels along the length of the dispensed tape to press the length of dispensed tape against the test surface; and
   means to remove the tape from the test surface.

2. The device according to claim 1, wherein the means to remove the tape includes a take-up spool for receiving the tape removed from the test surface.

3. The device according to claim 2, wherein the take-up spool includes a removable spool core adapted to receive the tape removed from the test surface.

4. The device according to claim 1, wherein the source of the tape is rotatatably mounted.

5. The device according to claim 2, including a plurality of guides for directing the tape dispensed from the source to the take-up spool.

6. The device according to claim 1, wherein the tape dispenser is adapted to dispense a length of the tape from the source.

7. The device according to claim 6, wherein the tape dispenser includes a rack mounted to provide a defined path of travel for the tape.

8. The device according to claim 1, wherein the brush is generally cylindrically shaped.

9. The device according to claim 8, wherein the brush includes helically mounted bristles.

10. The device according to claim 8, wherein the brush is rotatably mounted to the tape dispenser.

11. The device according to claim 7, including a pinion gear cooperating with the rack to cause a rotation of the brush.

12. The device according to claim 2, wherein the means to remove the tape includes a take-up lever having an associated gear segment engaged with a drive gear connected to the take-up spool.

13. The device according to claim 12, including a roller adapted to move upon a movement of the take-up lever.

14. The device according to claim 12, including a release lever, wherein a movement of the release lever releases the take-up lever from a normally locked position.

15. A device for testing the adhesion of a coating to a substrate comprising:
 a support;
 a dispensing spool rotatably mounted on the support and adapted to receive a roll of a pressure sensitive adhesive tape;
 a tape dispenser adapted to dispense a length of the tape from the dispensing spool; the dispenser including a slidable plate, a pinion gear, and a brush mounted thereto; and a rack to provide a defined path of travel for the plate, wherein the rack and the pinion gear cooperate to cause a rotation of the brush upon movement of the plate; the brush traveling along the length of the dispensed tape and causing the tape to contact a test surface disposed between the sidewalls of the support; and
 means to remove the tape from the test surface including a take-up spool having a drive gear and an associated gear segment, the gear segment engaged with the drive gear to cause rotation of the take-up spool to remove the tape from the test surface, the take-up spool receiving the tape removed from the test surface.

16. The device according to claim 15, including a plurality of guides for directing the tape dispensed from the dispensing spool to the take-up spool.

17. The adhesion testing device according to claim 15, including a roller moveably mounted on the support, wherein a movement of the roller causes the tape to be removed from the test surface at about a 180 degree angle in respect of a direction the tape is applied.

18. A method of testing the adhesion of a coating to a substrate comprising the steps of:
 providing a testing device having a support; a source of a pressure sensitive adhesive tape mounted to the support; a tape dispenser including a brush that travels along the length of the dispensed tape to press the length of dispensed tape against the test surface; and means to remove the dispensed tape from the test surface;
 dispensing the length of tape from the source;
 positioning the testing device to cause an adhesive side of at least a portion of the length of dispensed tape to contact the test surface;
 forcing the adhesive side of the tape against the test surface; and
 removing the length of tape from the test surface.

19. The method according to claim 18, including at least one of the steps of:
 inspecting one of the adhesive side of the length of tape removed from the test surface and the test surface for coating removed from the substrate; and
 rating the adhesion level of the coating to the substrate based on coating removed from the substrate by the tape.

* * * * *